(12) United States Patent
Lu et al.

(10) Patent No.: US 7,543,582 B2
(45) Date of Patent: Jun. 9, 2009

(54) DOSE INDICATING DEVICE WITH DISPLAY ELEMENTS ATTACHED TO CONTAINER

(75) Inventors: Winston Z. Lu, Kitchener (CA); Robert W. Morton, London (CA)

(73) Assignee: Trudell Medical International, London (CA)

( * ) Notice: Subject to any disclaimer, the term of this patent is extended or adjusted under 35 U.S.C. 154(b) by 604 days.

(21) Appl. No.: 11/226,688

(22) Filed: Sep. 14, 2005

(65) Prior Publication Data

US 2006/0060192 A1   Mar. 23, 2006

Related U.S. Application Data

(60) Provisional application No. 60/611,788, filed on Sep. 20, 2004.

(51) Int. Cl.
*A61M 11/00* (2006.01)

(52) U.S. Cl. .............................. 128/200.23; 128/205.23; 222/36

(58) Field of Classification Search ............ 128/205.23, 128/200.23, 203.12, 203.15; 222/36, 38, 222/48
See application file for complete search history.

(56) References Cited

U.S. PATENT DOCUMENTS

| | | | |
|---|---|---|---|
| 165,054 A | 6/1875 | Baldwin | |
| 498,851 A | 6/1893 | Jones | |
| 1,219,858 A | 3/1917 | Patterson | |
| 2,455,962 A | 12/1948 | Wheeler et al. | |
| 2,580,292 A | 12/1951 | Geary et al. | |
| 2,587,147 A | 2/1952 | Guion et al. | |
| 2,630,027 A | 3/1953 | Wunderlich | |
| 2,644,452 A | 7/1953 | Brown | |
| 2,767,680 A | 10/1956 | Lermer | |
| 2,770,711 A | 11/1956 | Baranowski | |
| 2,841,190 A | 7/1958 | Sheck | |
| 2,883,086 A | 4/1959 | Davison et al. | |
| 2,939,597 A | 6/1960 | Greene | |
| 2,943,730 A | 7/1960 | Tregilgas | |
| 2,953,242 A | 9/1960 | Shaw | |
| 3,001,524 A | 9/1961 | Maison et al. | |
| 3,073,468 A | 1/1963 | Arneson | |
| 3,085,745 A | 4/1963 | Auberger | |
| 3,119,557 A | 1/1964 | Chapman | |

(Continued)

FOREIGN PATENT DOCUMENTS

AU     598250 B2     6/1990

(Continued)

OTHER PUBLICATIONS

International Search Report in International Application No. PCT/IB2005/002764, dated Feb. 21, 2006, 8 pages.

(Continued)

*Primary Examiner*—Steven O Douglas
(74) *Attorney, Agent, or Firm*—Brinks Hofer Gilson & Lione

(57) ABSTRACT

An indicating device includes an indicating portion and an actuator portion. At least a part of the indicating portion is moveable with a container between engaged and disengaged positions relative to a dispenser housing. The indicating portion includes at least one indicator member. The container is moveable relative to the at least one indicator member along the longitudinal axis when the container is in the engaged position.

22 Claims, 4 Drawing Sheets

U.S. PATENT DOCUMENTS

| | | |
|---|---|---|
| 3,120,318 A | 2/1964 | Rigor |
| 3,148,801 A | 9/1964 | Radeloff et al. |
| 3,151,599 A | 10/1964 | Livingston |
| 3,170,597 A | 2/1965 | Reichenberger |
| 3,187,963 A | 6/1965 | Anderson |
| 3,189,232 A | 6/1965 | Joffe |
| 3,191,867 A | 6/1965 | Helms |
| 3,240,389 A | 3/1966 | Genua |
| 3,334,731 A | 8/1967 | Dale |
| 3,344,951 A | 10/1967 | Gervais |
| 3,361,306 A | 1/1968 | Grim |
| 3,402,863 A | 9/1968 | Green |
| 3,419,187 A | 12/1968 | Bazarnic |
| 3,446,179 A | 5/1969 | Bender |
| 3,477,561 A | 11/1969 | Espinal |
| 3,495,567 A | 2/1970 | Hayes et al. |
| 3,511,409 A | 5/1970 | Huck |
| 3,549,057 A | 12/1970 | Perez |
| 3,568,629 A | 3/1971 | Porter |
| 3,572,282 A | 3/1971 | Trump et al. |
| 3,589,563 A | 6/1971 | Carragan et al. |
| 3,612,349 A | 10/1971 | Thomas |
| 3,654,890 A | 4/1972 | Rigney et al. |
| 3,655,952 A | 4/1972 | Johnson et al. |
| 3,688,945 A | 9/1972 | Harman, Jr. et al. |
| 3,753,417 A | 8/1973 | Garby |
| 3,766,882 A | 10/1973 | Babbitt, III |
| 3,789,843 A | 2/1974 | Armstrong et al. |
| 3,792,242 A | 2/1974 | Hanson |
| 3,796,348 A | 3/1974 | Zipper |
| 3,797,748 A | 3/1974 | Nozawa et al. |
| 3,802,608 A | 4/1974 | Gullett |
| 3,831,808 A | 8/1974 | Bender |
| 3,831,812 A | 8/1974 | Dolan |
| 3,845,883 A | 11/1974 | Johnson et al. |
| 3,848,774 A | 11/1974 | Schimke |
| 3,886,879 A | 6/1975 | Frost et al. |
| 3,887,099 A | 6/1975 | Gillman et al. |
| 3,921,568 A | 11/1975 | Fish |
| 3,926,326 A | 12/1975 | Grau |
| 3,950,939 A | 4/1976 | Meisner |
| 3,960,713 A | 6/1976 | Carey |
| 3,977,554 A | 8/1976 | Costa |
| 3,994,421 A | 11/1976 | Hansen |
| 4,011,829 A | 3/1977 | Wachsmann et al. |
| 4,029,033 A | 6/1977 | Kerwin et al. |
| 4,034,757 A | 7/1977 | Glover |
| 4,037,719 A | 7/1977 | Perlmutter |
| 4,069,935 A | 1/1978 | Hampel |
| 4,069,942 A | 1/1978 | Marshall et al. |
| 4,078,661 A | 3/1978 | Thomas |
| 4,094,408 A | 6/1978 | Ford |
| 4,162,746 A | 7/1979 | Anderson et al. |
| 4,164,301 A | 8/1979 | Thayer |
| 4,188,984 A | 2/1980 | Lyall |
| 4,220,247 A | 9/1980 | Kramer |
| 4,291,688 A | 9/1981 | Kistler |
| 4,300,548 A | 11/1981 | Jones |
| 4,319,128 A | 3/1982 | Dow, Jr. et al. |
| 4,345,541 A | 8/1982 | Villa-Real |
| 4,347,804 A | 9/1982 | Villa-Real |
| 4,347,853 A | 9/1982 | Gereg et al. |
| 4,350,265 A | 9/1982 | Griffiths et al. |
| 4,354,621 A | 10/1982 | Knickerbocker |
| 4,357,192 A | 11/1982 | Moser |
| 4,365,722 A | 12/1982 | Kramer |
| 4,368,381 A | 1/1983 | Ishiyama |
| 4,405,045 A | 9/1983 | Villa-Real |
| 4,419,016 A | 12/1983 | Zoltan |
| 4,432,300 A | 2/1984 | Lyss |
| 4,436,223 A | 3/1984 | Wilson |
| 4,440,306 A | 4/1984 | Van Buskirk et al. |
| 4,489,834 A | 12/1984 | Thackrey |
| 4,500,005 A | 2/1985 | Forrester |
| 4,501,370 A | 2/1985 | Kelley |
| 4,511,150 A | 4/1985 | Seguenot |
| 4,523,933 A | 6/1985 | Laush et al. |
| 4,528,933 A | 7/1985 | Allen |
| 4,534,345 A | 8/1985 | Wetterlin |
| 4,538,744 A | 9/1985 | Weissenborn |
| 4,548,157 A | 10/1985 | Hevoyan |
| 4,562,933 A | 1/1986 | Dennis |
| 4,565,302 A | 1/1986 | Pfeiffer et al. |
| 4,599,508 A | 7/1986 | Smetaniuk |
| 4,634,012 A | 1/1987 | Kelley |
| 4,637,528 A | 1/1987 | Wachinski et al. |
| 4,641,759 A | 2/1987 | Kelley |
| 4,646,936 A | 3/1987 | Frazier et al. |
| 4,662,520 A | 5/1987 | Griffin |
| 4,664,107 A | 5/1987 | Wass |
| 4,666,051 A | 5/1987 | Trick |
| 4,668,218 A | 5/1987 | Virtanen |
| 4,677,975 A | 7/1987 | Edgar et al. |
| 4,693,399 A | 9/1987 | Hickman et al. |
| 4,705,182 A | 11/1987 | Newell-Lewis |
| 4,722,729 A | 2/1988 | Dettbarn et al. |
| 4,723,673 A | 2/1988 | Tartaglia et al. |
| 4,727,886 A | 3/1988 | Conrardy et al. |
| 4,736,871 A | 4/1988 | Luciani et al. |
| 4,749,093 A | 6/1988 | Trick |
| 4,753,189 A | 6/1988 | Mastman et al. |
| 4,756,423 A | 7/1988 | Holtsch |
| 4,782,966 A | 11/1988 | Thackrey |
| 4,792,664 A | 12/1988 | Schwab |
| 4,817,822 A | 4/1989 | Rand et al. |
| 4,890,572 A | 1/1990 | Huang |
| 4,934,358 A | 6/1990 | Nilsson et al. |
| 4,934,568 A | 6/1990 | Fuchs |
| 4,947,875 A | 8/1990 | Brooks et al. |
| 4,955,371 A | 9/1990 | Zamba et al. |
| 4,969,578 A | 11/1990 | Gander et al. |
| 4,973,250 A | 11/1990 | Milman |
| 4,984,158 A | 1/1991 | Hillsman |
| 5,009,338 A | 4/1991 | Barker |
| 5,011,032 A | 4/1991 | Rollman |
| 5,020,527 A | 6/1991 | Dessertine |
| 5,027,806 A | 7/1991 | Zoltan et al. |
| 5,027,808 A | 7/1991 | Rich et al. |
| 5,038,972 A | 8/1991 | Muderlak et al. |
| 5,060,643 A | 10/1991 | Rich et al. |
| 5,069,204 A | 12/1991 | Smith et al. |
| 5,082,129 A | 1/1992 | Kramer |
| 5,082,130 A | 1/1992 | Weinstein |
| 5,115,929 A | 5/1992 | Buono |
| 5,174,473 A | 12/1992 | Marelli |
| 5,184,761 A | 2/1993 | Lee |
| 5,188,251 A | 2/1993 | Kusz |
| 5,190,643 A | 3/1993 | Duncan et al. |
| 5,209,375 A | 5/1993 | Fuchs |
| 5,215,079 A | 6/1993 | Fine et al. |
| 5,217,004 A | 6/1993 | Blasnik et al. |
| 5,224,474 A | 7/1993 | Bloomfield |
| 5,227,764 A | 7/1993 | Umemoto |
| 5,228,586 A | 7/1993 | Fuchs |
| 5,242,067 A | 9/1993 | Garby et al. |
| 5,243,970 A | 9/1993 | Amrosio et al. |
| 5,261,548 A | 11/1993 | Barker et al. |
| 5,263,475 A | 11/1993 | Altermatt et al. |
| 5,284,133 A | 2/1994 | Burns et al. |
| 5,289,946 A | 3/1994 | Fuchs |
| 5,299,701 A | 4/1994 | Barker et al. |
| 5,300,042 A | 4/1994 | Kossoff et al. |
| 5,301,873 A | 4/1994 | Burke et al. |
| 5,328,597 A | 7/1994 | Boldt, Jr. et al. |

| | | | | | |
|---|---|---|---|---|---|
| 5,331,953 A | 7/1994 | Andersson et al. | 6,138,669 A | 10/2000 | Rocci, Jr. et al. |
| 5,335,823 A | 8/1994 | Fuchs et al. | 6,142,339 A | 11/2000 | Blacker et al. |
| 5,349,944 A | 9/1994 | Chippendale et al. | 6,148,815 A | 11/2000 | Wolf |
| 5,349,945 A | 9/1994 | Wass et al. | 6,149,054 A | 11/2000 | Cirrillo |
| 5,356,012 A | 10/1994 | Tang et al. | 6,155,251 A | 12/2000 | Hauser |
| 5,363,842 A | 11/1994 | Mishelevich et al. | 6,161,724 A | 12/2000 | Blacker et al. |
| 5,370,267 A | 12/1994 | Schroeder | 6,164,494 A | 12/2000 | Marelli |
| 5,382,243 A | 1/1995 | Mulholland | 6,186,364 B1 | 2/2001 | Dobbs |
| RE34,847 E | 2/1995 | Muderlak et al. | 6,202,642 B1 | 3/2001 | McKinnon et al. |
| 5,388,572 A | 2/1995 | Mulhauser et al. | 6,223,744 B1 | 5/2001 | Garon |
| 5,392,768 A | 2/1995 | Johansson et al. | 6,234,168 B1 | 5/2001 | Bruna |
| 5,394,866 A | 3/1995 | Ritson et al. | 6,283,365 B1 | 9/2001 | Bason |
| 5,397,028 A | 3/1995 | Jesadanont | 6,328,037 B1 | 12/2001 | Scarrott et al. |
| 5,411,173 A | 5/1995 | Weinstein | 6,336,453 B1 | 1/2002 | Scarrott et al. |
| 5,421,482 A | 6/1995 | Garby et al. | 6,360,739 B1 | 3/2002 | Rand et al. |
| 5,437,270 A | 8/1995 | Braithwaite | 6,405,727 B1 | 6/2002 | MacMichael et al. |
| 5,447,150 A | 9/1995 | Bacon | 6,415,785 B1 | 7/2002 | Stage |
| 5,448,042 A | 9/1995 | Robinson et al. | 6,425,392 B1 | 7/2002 | Sosiak |
| 5,482,030 A | 1/1996 | Klein | 6,431,168 B1 | 8/2002 | Rand et al. |
| 5,482,163 A | 1/1996 | Hoffman | 6,435,372 B1 | 8/2002 | Blacker et al. |
| 5,505,192 A | 4/1996 | Samiotes et al. | 6,446,627 B1 | 9/2002 | Bowman et al. |
| 5,505,195 A | 4/1996 | Wolf et al. | 6,474,331 B1 | 11/2002 | Rand et al. |
| 5,509,905 A | 4/1996 | Michel | 6,481,438 B1 | 11/2002 | Gallem et al. |
| 5,519,197 A | 5/1996 | Robinson et al. | 6,484,717 B1 | 11/2002 | Dagsland et al. |
| 5,520,166 A | 5/1996 | Ritson et al. | 6,516,799 B1 | 2/2003 | Greenwood et al. |
| 5,522,378 A | 6/1996 | Ritson et al. | 6,529,446 B1 | 3/2003 | de la Huerga |
| 5,544,647 A | 8/1996 | Jewett et al. | 6,561,384 B2 | 5/2003 | Blacker et al. |
| 5,549,101 A | 8/1996 | Trofast et al. | 6,601,582 B2 | 8/2003 | Rand et al. |
| 5,564,414 A | 10/1996 | Walker et al. | 6,615,827 B2 | 9/2003 | Greenwood et al. |
| 5,574,268 A | 11/1996 | Herman et al. | 6,659,307 B1 | 12/2003 | Stradella |
| 5,611,444 A | 3/1997 | Garby et al. | 6,679,251 B1 | 1/2004 | Gallem et al. |
| 5,617,844 A | 4/1997 | King | 6,701,917 B2 | 3/2004 | O'Leary |
| 5,622,163 A | 4/1997 | Jewett et al. | 6,718,972 B2 | 4/2004 | O'Leary |
| 5,625,334 A | 4/1997 | Compton | 6,729,330 B2 | 5/2004 | Scarrott et al. |
| 5,625,659 A | 4/1997 | Sears | 6,752,153 B1 | 6/2004 | Eckert |
| 5,638,970 A | 6/1997 | Garby et al. | 6,761,161 B2 | 7/2004 | Scarrott et al. |
| 5,657,748 A | 8/1997 | Braithwaite | 6,766,799 B2 | 7/2004 | Edwards et al. |
| 5,676,129 A | 10/1997 | Rocci, Jr. et al. | 6,769,601 B2 | 8/2004 | Haikarainen et al. |
| 5,687,710 A | 11/1997 | Ambrosio et al. | 6,907,876 B1 | 6/2005 | Clark et al. |
| 5,692,492 A | 12/1997 | Bruna et al. | 7,004,164 B2 | 2/2006 | Scarrott |
| 5,694,882 A | 12/1997 | Marshall | 7,137,391 B2 | 11/2006 | Bruna |
| 5,718,355 A | 2/1998 | Garby et al. | 7,143,764 B1 | 12/2006 | Dagsland et al. |
| 5,724,957 A | 3/1998 | Rubsamen et al. | 7,156,258 B2 * | 1/2007 | Eckert .................. 222/23 |
| 5,732,836 A | 3/1998 | Barker et al. | 2002/0000225 A1 | 1/2002 | Schuler et al. |
| 5,740,792 A | 4/1998 | Ashley et al. | 2002/0153005 A1 | 10/2002 | Scarrott et al. |
| 5,758,638 A | 6/1998 | Kreamer | 2003/0183225 A1 | 10/2003 | Knudsen |
| 5,772,074 A | 6/1998 | Dial et al. | 2003/0200964 A1 | 10/2003 | Blakley et al. |
| 5,794,612 A | 8/1998 | Wachter et al. | 2003/0209239 A1 | 11/2003 | Rand et al. |
| 5,799,651 A | 9/1998 | Garby et al. | 2004/0065326 A1 | 4/2004 | MacMichael et al. |
| 5,803,283 A | 9/1998 | Barker et al. | 2004/0069301 A1 | 4/2004 | Bacon |
| 5,809,997 A | 9/1998 | Wolf | 2004/0094147 A1 | 5/2004 | Schyra et al. |
| 5,826,571 A | 10/1998 | Casper et al. | 2004/0144798 A1 | 7/2004 | Ouyang et al. |
| 5,829,434 A | 11/1998 | Ambrosio et al. | 2004/0149772 A1 | 8/2004 | Ouyang |
| 5,845,777 A | 12/1998 | Najmi | 2004/0149773 A1 | 8/2004 | Ouyang et al. |
| 5,852,590 A | 12/1998 | de la Huerga | 2004/0221840 A1 | 11/2004 | Stockman-Lamb |
| 5,871,007 A | 2/1999 | Clark, Jr. | 2004/0255935 A1 | 12/2004 | Bruna |
| 5,873,995 A | 2/1999 | Huang et al. | 2004/0255936 A1 | 12/2004 | Urbanus |
| 5,882,507 A | 3/1999 | Tanner et al. | 2005/0011515 A1 | 1/2005 | Lee et al. |
| 5,896,855 A | 4/1999 | Hobbs | 2005/0056276 A1 | 3/2005 | Schuler et al. |
| 5,896,990 A | 4/1999 | Barzana | 2005/0268905 A1 | 12/2005 | Rasmussen et al. |
| 5,899,201 A | 5/1999 | Schultz et al. | 2005/0284471 A1 | 12/2005 | Bruna |
| 5,904,139 A | 5/1999 | Hauser | 2006/0254581 A1 | 11/2006 | Genova et al. |
| 5,957,896 A | 9/1999 | Bendek et al. | | | |
| 5,988,496 A | 11/1999 | Bruna | | FOREIGN PATENT DOCUMENTS | |
| 6,000,159 A | 12/1999 | Hornung | | | |
| 6,012,450 A | 1/2000 | Rubsamen | CA | 535518 | 1/1957 |
| 6,029,659 A | 2/2000 | O'Connor | CA | 2 152 088 A | 7/1994 |
| 6,059,133 A | 5/2000 | Lai | CA | 2 181 789 C | 6/1996 |
| 6,062,214 A | 5/2000 | Howlett | CA | 2 190 204 C | 5/1997 |
| 6,076,521 A | 6/2000 | Lindahl et al. | CA | 2 293 484 A | 12/1998 |
| 6,082,358 A | 7/2000 | Scarrott et al. | CA | 2 486 892 A1 | 12/1998 |
| 6,089,180 A | 7/2000 | Nichols, Jr. | CA | 2 315 777 A1 | 7/1999 |
| 6,119,684 A | 9/2000 | Nohl et al. | CA | 2 331 179 A1 | 11/1999 |

| | | |
|---|---|---|
| CA | 2 383 425 A1 | 3/2001 |
| CA | 2 388 958 A1 | 3/2001 |
| CA | 2 414 118 A1 | 1/2002 |
| CA | 2 420 171 A1 | 3/2002 |
| CA | 2 480 035 A1 | 10/2003 |
| DE | 6 603 758 | 7/1969 |
| DE | 27 02 539 A1 | 1/1977 |
| DE | 33 36 486 A1 | 4/1984 |
| DE | G 85 90 143.1 | 10/1985 |
| DE | G 86 02 238.5 | 5/1986 |
| EP | 0 028 929 A2 | 5/1981 |
| EP | 0 098 939 A2 | 1/1984 |
| EP | 0 114 617 A2 | 8/1984 |
| EP | 0 063 599 | 6/1986 |
| EP | 0 230 323 B1 | 7/1987 |
| EP | 0 236 871 A2 | 9/1987 |
| EP | 0 269 496 A2 | 6/1988 |
| EP | 0 280 104 B1 | 8/1988 |
| EP | 0 488 609 A1 | 6/1992 |
| EP | 0 559 757 B1 | 9/1993 |
| EP | 0 949 584 A2 | 10/1999 |
| EP | 1 369 139 A1 | 12/2003 |
| EP | 1 220 802 B1 | 2/2004 |
| FR | 2 743 055 | 7/1997 |
| GB | 998 148 | 7/1965 |
| GB | 1 058 636 | 2/1967 |
| GB | 1 290 484 | 9/1972 |
| GB | 1 317 315 | 5/1973 |
| GB | 2 036 695 A | 7/1980 |
| GB | 2 063 075 A | 6/1981 |
| GB | 2 092 991 A | 8/1982 |
| GB | 2 104 393 A | 3/1983 |
| GB | 2 191 032 A | 12/1987 |
| GB | 2 195 544 A | 4/1988 |
| GB | 2 348 928 A | 10/2000 |
| GB | 2 372 543 A | 8/2002 |
| GB | 2 414 187 A | 11/2005 |
| JP | 6-26891 | 4/1994 |
| WO | WO 86/02275 | 4/1986 |
| WO | WO 87/04354 | 8/1987 |
| WO | WO 90/10470 | 9/1990 |
| WO | WO 91/06334 | 5/1991 |
| WO | WO 92/07600 | 5/1992 |
| WO | WO 92/09324 | 6/1992 |
| WO | WO 92/15353 | 9/1992 |
| WO | WO 92/17231 | 10/1992 |
| WO | WO 93/24167 | 12/1993 |
| WO | WO 94/11272 | 5/1994 |
| WO | WO 94/14492 | 7/1994 |
| WO | WO 95/34874 | 12/1995 |
| WO | WO 96/16686 | 6/1996 |
| WO | WO 96/16687 | 6/1996 |
| WO | WO 96/39337 | 12/1996 |
| WO | WO 98/01822 | 1/1998 |
| WO | WO 98/56444 | 12/1998 |
| WO | WO 98/56445 | 12/1998 |
| WO | WO 99/36115 | 7/1999 |
| WO | WO 99/57019 | 11/1999 |
| WO | WO 00/09187 | 2/2000 |
| WO | WO 00/59806 | 10/2000 |
| WO | WO 01/28887 A1 | 4/2001 |
| WO | WO 01/29765 A1 | 4/2001 |
| WO | WO 01/37909 A1 | 5/2001 |
| WO | WO 03/101514 A1 | 12/2003 |
| WO | WO 03/103759 A1 | 12/2003 |
| WO | WO 2004/089451 A1 | 10/2004 |
| WO | WO 2006/110080 A1 | 10/2006 |

OTHER PUBLICATIONS

Written Opinion in International Application No. PCT/IB2005/002764, dated Feb. 21, 2006, 5 pages.

U.S. Department of Health and Human Services, Food and Drug Administration, Center for Drug Evaluation and Research (CDER)—Clinical, "Guidance for Industry: Integration of Dose-Counting Mechanisms into MDI Drug Products—Draft Guidance," dated Nov. 2001, 6 pages.

* cited by examiner

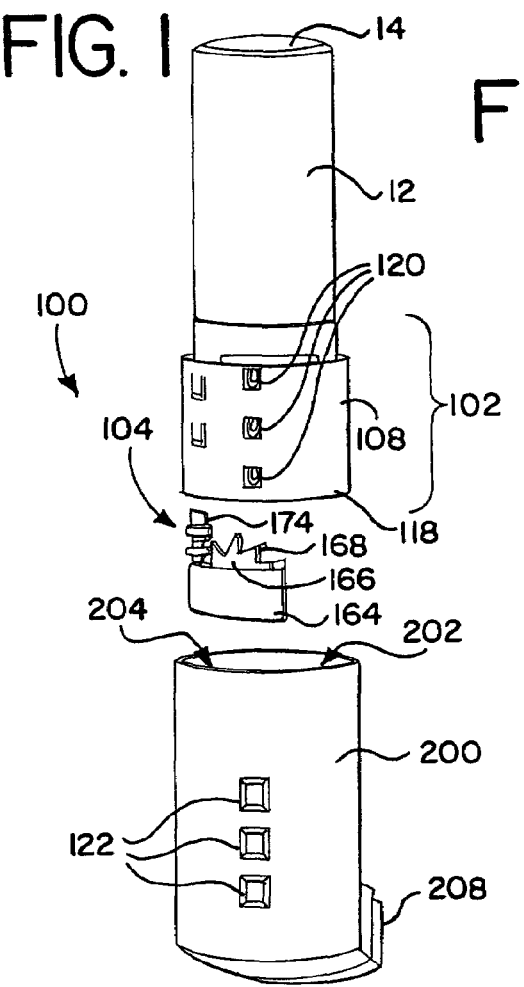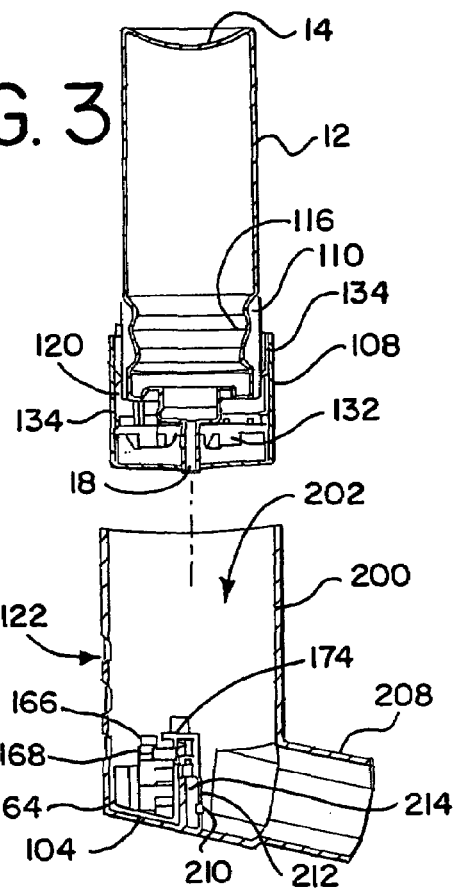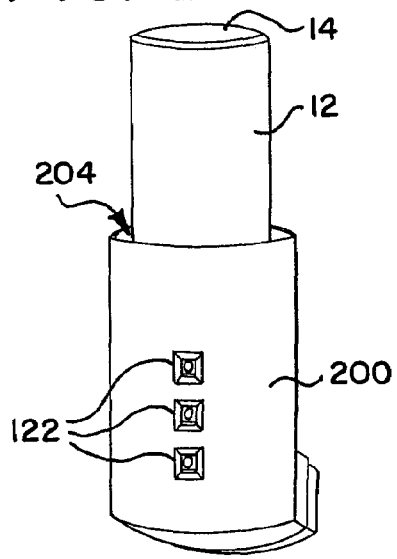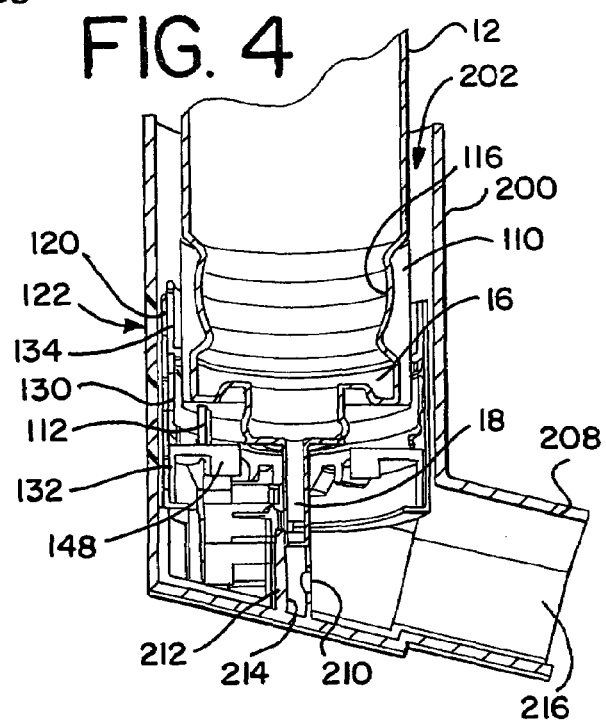

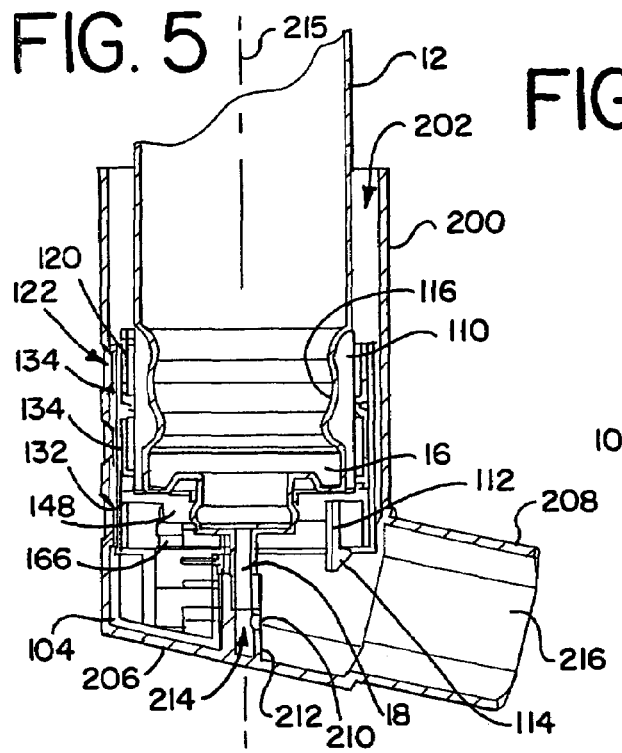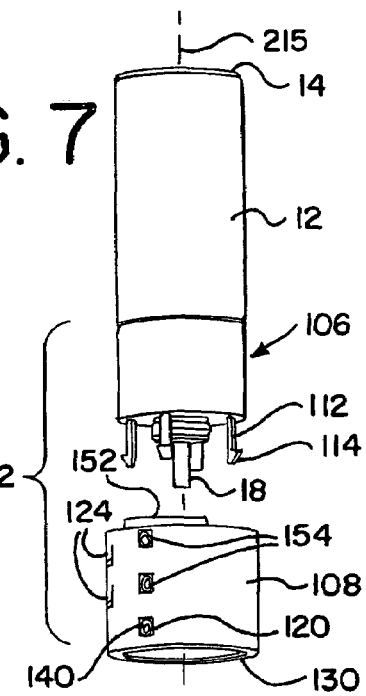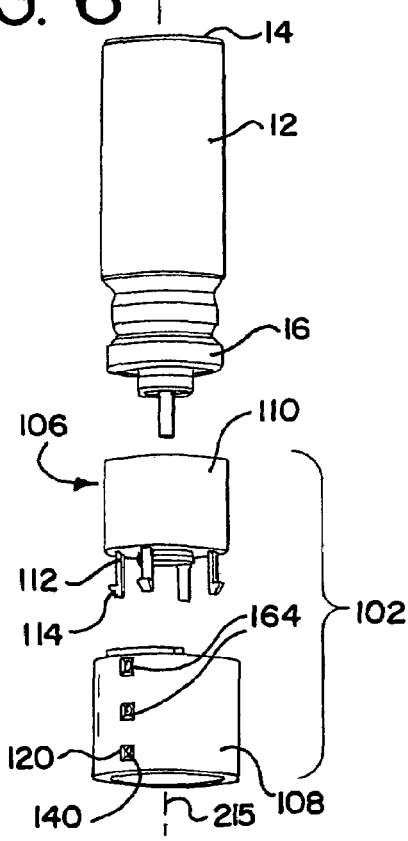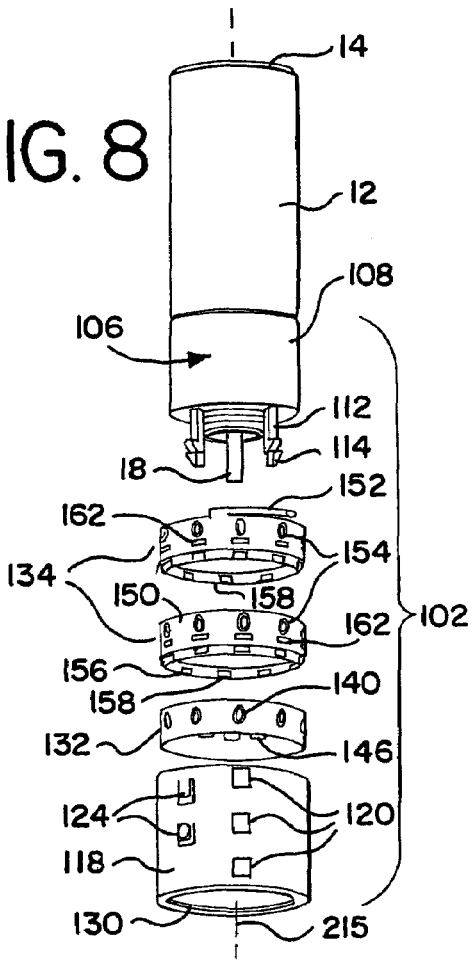

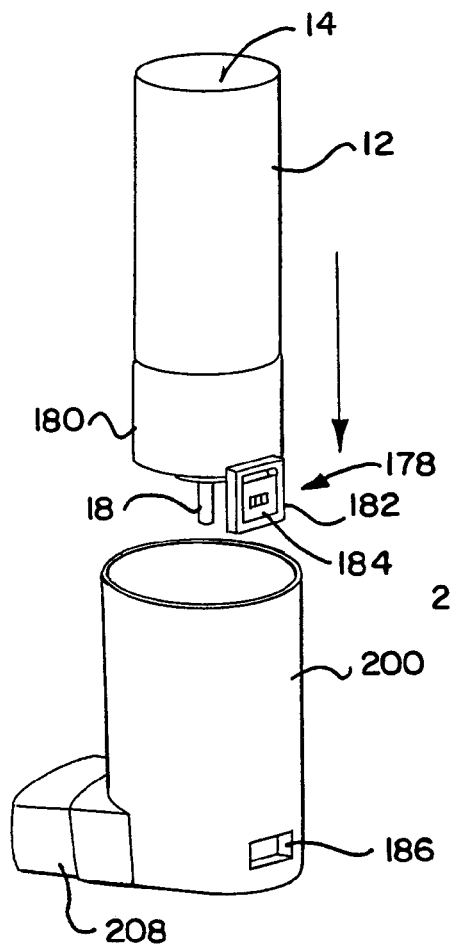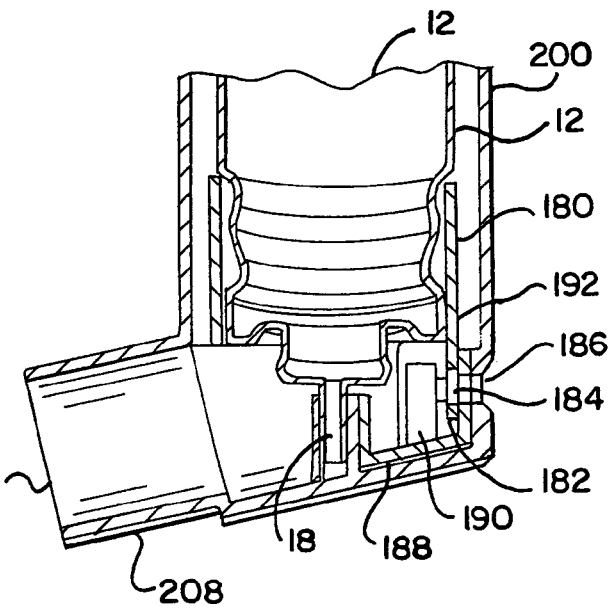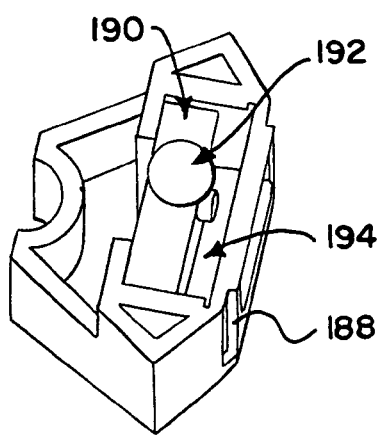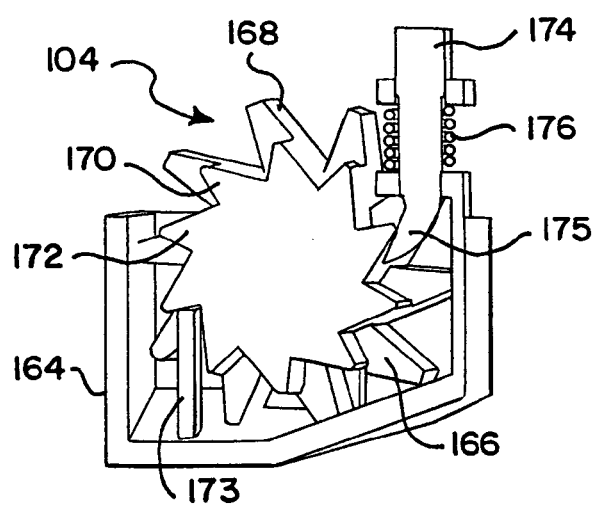

DOSE INDICATING DEVICE WITH DISPLAY ELEMENTS ATTACHED TO CONTAINER

This application claims the benefit of U.S. Provisional Application No. 60/611,788, filed Sep. 20, 2004, the entire disclosure of which is hereby incorporated herein by reference.

BACKGROUND

The present invention relates generally to an indicating device for indicating the number of dosages that have been dispensed from or remain in a container, and in particular to a dose indicating device having display elements attached to the container.

Aerosol dispensing devices have been developed that include a dose indicating device to indicate the number of metered doses that have been dispensed from the device, or to indicate the number of doses remaining therein. For example, patients have certain conditions that can be treated with medicaments dispensed in an aerosol and administered to the patient by inhalation. In one format, the aerosol with medicaments are contained in a container, and dispensed in metered, or measured, dosages with an inhalation device, or actuator boot. In such an arrangement, it can be important for the patient to be able to ascertain the number of metered doses remaining in the container, either by an indication of the number remaining therein or by knowledge of the number already dispensed therefrom, such that the patient is not caught unaware with an empty container when in need of the medicament. Thus, it may be important for the inhalation device to provide an accurate indication of either the number of doses remaining in the container, or the number of doses already dispensed therefrom.

Typically, a conventional aerosol container includes a body and a valve stem that can be depressed relative to the body so as to emit the metered dose of aerosol and medicament. The container typically is supplied with a predetermined number of metered doses, generally on the order of about 200, such that the counting of the number of valve stem depressions, and corresponding number of dispensed metered doses, can be directly correlated with the number of doses remaining in the container.

In operation, the container is typically received within a housing of the inhalation device, wherein the valve is brought into engagement with a support block in the housing. The user administers the medicament by moving the container relative to the housing so as to depress the valve stem and internal valve and thereby release a metered dose, which is typically administered to the user through a port or mouthpiece extending from the housing. After the dose is administered, the valve stem, which is typically spring loaded, biases the container away from the support block so as to again move the container relative to the housing. In this way, a metered dose of medicament is administered by each cycle of linear reciprocal movement of the container relative to the housing.

Some actuator boots, or other devices attached to the medicament container, have indicating devices that convert the linear reciprocal movement of the container relative to the housing into a one-way, or single-cycle, movement of an indicator, wherein the indicator identifies the relative fullness of the container, the number of metered doses remaining therein or the number of doses already administered. Often, the indicator is disposed inside the actuator boot. If the container is removed from the actuator boot, for example to clean the actuator boot, a different container may inadvertently be inserted into the actuator boot, thereby corrupting the count.

To solve this problem, some devices, including the indicator, are secured to the container, as shown for example in U.S. Pat. No. 6,431,168 to Rand. In the '168 patent to Rand, however, the indicators move with the container as it moves relative to the actuator boot. Therefore, the indicator member moves relative to the viewing window in the actuator boot, which can be a distraction and can create confusion and difficulties in reading the device, thereby calling into question the accuracy and robustness of the device.

SUMMARY

Briefly stated, in one preferred embodiment, a dispenser assembly includes a dispenser housing and a container having an end portion and a valve moveable between a closed position and an open position. The container dispenses metered dosages of substance when the valve is moved to the open position. The container is moveable relative to the dispenser housing between an engaged position and a disengaged position. The container is removeably connected to the dispenser housing and is moveable relative to the dispenser housing along a longitudinal axis when in the engaged position. The container is disconnected from the dispenser housing when in the disengaged position. An indicating device includes an indicating portion and an actuator portion. At least a part of the indicating portion is moveable with the container between the engaged and disengaged positions. The indicating portion includes at least one indicator member. The container is moveable relative to the at least one indicator member along the longitudinal axis when the container is in the engaged position.

In one embodiment, the actuator portion is connected to the dispenser housing and remains connected thereto as the container and indicating portion are moved from the engaged position to the disengaged position.

In another aspect, an indicating device kit is provided. The kit includes an indicator portion and an actuator portion.

Methods for indicating the number of metered dosages of substance dispensed from or remaining in the container using the various embodiments are also provided.

The various embodiments provide simple, robust and inexpensive solutions for providing the user with information allowing them to ascertain the number of metered doses remaining in the container, either by an indication of the number remaining therein or by knowledge of the number already dispensed therefrom. In addition, the indicating portion remains with the container, even if it is removed from the dispenser housing, thereby ensuring that the integrity of the dose count for the container is preserved. At the same time, the indicator is moveable relative to the container along the longitudinal axis, such that it can remain visible in the viewing window of the dispenser housing.

The foregoing paragraphs have been provided by way of general introduction, and are not intended to limit the scope of the following claims. The various preferred embodiments, together with further advantages, will be best understood by reference to the following detailed description taken in conjunction with the accompanying drawings.

BRIEF DESCRIPTION OF THE DRAWINGS

FIG. 1 is an exploded perspective view of a dispenser including a container and dose indicating device.

FIG. 2 is a perspective view of the assembled dispenser, including the dose indicating device, shown in FIG. 1.

FIG. 3 is a side, cross-sectional view of a container with an indicator portion secured thereto in a disengaged position relative to a dispenser housing and actuator portion disposed therein.

FIG. 4 is a side, cross-sectional view of the container and indicator portion mounted to the dispenser housing, with the container valve stem in an extended position.

FIG. 5 is a side, cross-sectional view of the container and indicator portion mounted to the dispenser housing shown in FIG. 4, with the container valve stem in a depressed position.

FIG. 6 is an exploded perspective view of a container with a retaining collar mounted thereon positioned adjacent an indicator portion housing with a plurality of indicator members.

FIG. 7 is a perspective view of the container, retaining collar and indicator portion housing shown in FIG. 6.

FIG. 8 is an exploded perspective view of a container with a retaining collar mounted thereon, an indicator portion housing and a plurality of indicator members.

FIG. 13 is a perspective view of a container with an indicator portion including a LCD screen in a disengaged position relative to a dispenser housing.

FIG. 14 is an enlarged cross-sectional view of the container and indicator portion show in FIG. 13 in an engaged position relative to the dispenser housing.

FIG. 15 is a top perspective view of the actuator portion shown in FIG. 14.

FIG. 16 is a partial cross-sectional side view of the actuator portion shown in FIG. 12.

DETAILED DESCRIPTION OF THE PRESENTLY PREFERRED EMBODIMENTS

Figure 9:
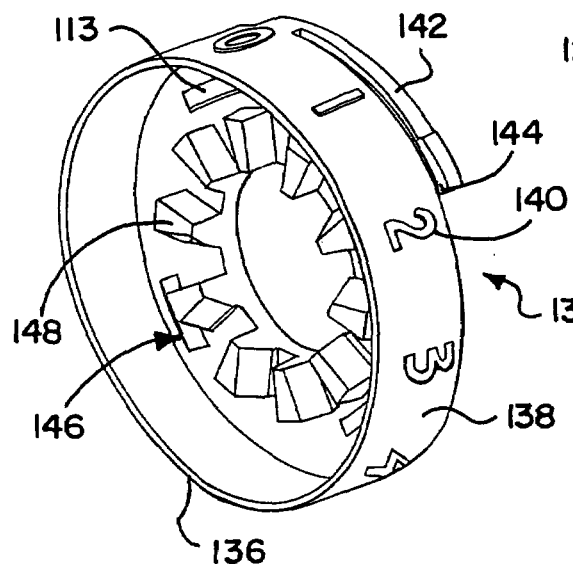
FIG. 9 is a bottom perspective view of a first indicator member.

General Description of Dispenser:

Referring to the drawings, and in particular FIGS. 1-5, an aerosol dispenser is shown as including a housing 200, or actuator boot, and a container 12 disposed therein. The housing has a longitudinally extending cavity 202 shaped to receive the container. A top portion of the housing is generally open such that the container can be inserted in the housing through an opening 204 and installed therein with a bottom end 14 of the container protruding from the housing so as to be exposed to the user for actuation.

The terms "longitudinal" and "axial" as used herein are intended to indicate the direction of the reciprocal movement of the container relative to the housing, and of an indicating device cap member relative to a base member. The terms "top," "bottom," "upwardly" and "downwardly" are intended to indicate directions when viewing the inhalation devices as shown in the Figures, but with the understanding that the container is inverted such that the top surface thereof is located adjacent the bottom of the housing and vice versa. Moreover, it should be understood that a user can use the container and dispenser in any number of positions, including but not limited to the preferred upright position shown in FIG. 2. The terms "connect," "connected," "couple," and "coupled," and equivalents thereof, refers to the connection of two components directly, or indirectly, i.e., by way of one or more intervening components.

As shown in FIGS. 3-5, a cylindrical support block 212 having a well 214 is formed in a bottom portion 206 of the housing. An orifice 210 penetrates the support block to communicate with a bottom portion of the well. In one embodiment, a mouthpiece 208, intended for insertion into the mouth of a patient, forms an exhaust port 216 that communicates with the orifice and well. The mouthpiece 208 extends laterally from the housing so as to facilitate insertion of the mouthpiece into the mouth of the patient.

The container 12 is preferably cylindrical and has a hub 16 disposed on a top thereof. A valve stem 18 extends longitudinally from the hub. The valve stem extends coaxially from the container and is biased outwardly therefrom by a spring (not shown) mounted within the valve stem of the container. The container 12 is mounted in the housing by press fitting the valve stem 18 in the well 214 of the support block.

In a preferred embodiment, the container 12 is filled with a substance that is dispensed therefrom in specific metered doses by an actuation thereof effected by depressing or moving the valve stem 18 from an extended closed position to a depressed open position. Preferably the substance is a medicament, although it should be understood that the container may be used to hold a variety of non-medicinal substances, including, but not limited to, various liquids, foams or aerosols. In one preferred embodiment, the container is a pressurized, metered dose inhaler. A single metered dose is dispensed from the container by each reciprocal, longitudinal movement of the valve stem, or actuation of the container. It should also be understood that the valve system can be actuated by a variety of actuators, including, but not limited to, various pumps, levers, actuator boots, buttons and the like. In some embodiments, the container and valve system is breath-actuated, meaning they are actuated in response to the user inhaling, for example by inhaling through the mouthpiece. In such embodiments, the valve system can be actuated by an actuator moveable relative to the container and housing such that the container remains stationary relative to the housing.

In operation, the opening of the valve stem is effected by moving the container 12 reciprocally within the housing 200 along a longitudinal axis 215, defined by the valve stem and the reciprocal movement of the container, by depressing the bottom end 14 of the container relative to the housing so as to move the valve stem 18 to the open position as it is supported within the well by the support block. As the valve stem is moved to the open position, the container dispenses a metered dose of a substance through the well 214 and orifice 210. The substance, for example an aerosol and medicament, are then transmitted to the patient through an exhaust port 216 of the mouthpiece by 208 way of either a self-generated or assisted airflow.

In other delivery systems, the housing and holder for the container are attached to a component having a chamber with an output end. Examples of these kinds of delivery systems are shown for example in U.S. Pat. No. 5,012,803, issued May 7, 1991, and U.S. Pat. No. 4,460,412, issued Sep. 11, 1984, both of which are hereby incorporated herein by reference. (No license, expressed or implied, is intended to be granted to any patent by reason of the incorporation by reference herein). In these kinds of delivery systems, the component having the chamber can be adapted to receive the mouthpiece of the housing, or it can be integrally connected with a holder supporting the container. In either embodiment, the metered dose of medicament in aerosol is first dispensed from the container into the chamber, and thereafter inhaled by the patient.

In a preferred embodiment, the container 12 is intended to dispense a predetermined number of metered doses of a substance, such as a medicament, upon a corresponding number of predetermined actuations of the container. For example, conventional inhaler containers typically hold on the order of 100 to 200 metered doses. It should be understood, however, that the range of available doses could potentially vary from as few as one dose to as many as 500, or even more, depending, for example, on the capacity of the container, and/or the size of the metering dose valve. In operation, it can be important for the patient to be aware of the number of metered doses remaining in the container such that the patient is not caught unaware with an empty container when in need of the medicament.

Description of Indicating Device Disposed in Dispenser Housing and Operation Thereof:

Referring to FIGS. 1-5, an aerosol dispenser is shown as including the housing 200, the container 12 mounted therein as described above and an indicating device 100 having an indicating portion 102 and an actuator portion 104. The indicating portion includes a collar 106 and a housing 108. As shown in FIGS. 3-7, the collar includes a ring portion 110 and a plurality (shown as four) of longitudinally extending arms 112 each having a tab or hook portion 114 formed on a free end thereof. The ring portion 110 is secured around the top end of the container. The ring portion can include a longitudinal slit to allow it to be expanded and fitted around the end portion or ferrule of the container. The ring portion 110 can alternatively have a contoured interior surface 116, as shown in FIGS. 4 and 5, which allow it to be mated with and snap fit around the end portion of the container. The collar 106 is moveable with the container 12 relative to the dispenser housing 200 and actuator portion 104 of the indicating device.

Figure 11:
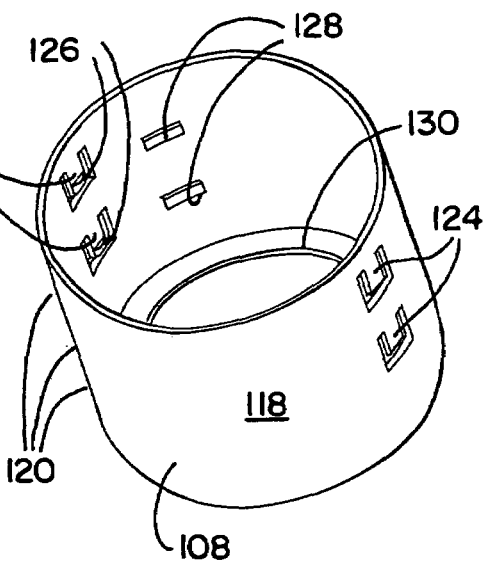
FIG. 11 is a top perspective view of an indicator portion housing.

The indicating portion housing 108, shown in FIGS. 1-8 and 11, has a cylindrical, longitudinally extending wall 118. A plurality of longitudinally spaced viewing windows 120 are disposed in said wall. The position of the viewing windows corresponds to and are aligned with a plurality of viewing windows 122 formed in the dispenser housing, as shown in FIGS. 1 and 2. Referring to FIG. 11, the housing further includes at least two pairs of a plurality (shown as two) of longitudinally spaced indexing portions 124. The indexing portions are configured as flexible arms and include a tooth or bump 126 that extends radially inward from a free end of an indexing portion arm. The housing 108 further includes a plurality (shown as two) of longitudinally spaced engagement portions 128, formed as protuberances or bumps on an interior surface of the housing wall. It should be understood that more or less than two indexing portions or engagement portions can be formed on the housing depending on the number of indicator members being used in the device. The housing includes a bottom lip 130 or ring that extends radially inward from a bottom of the wall.

Referring to FIGS. 3-5 and 8-10, the indicating portion further includes a plurality of indicator members 132, 134. Preferably, the indicator members are rotatable about the longitudinal axis 215. A first indicator member 132, shown in FIG. 9, has a bottom surface 136 that rests and slides along the top of the bottom lip 130 of the housing. The indicator member 132 has circumferential skirt 138 with indicia 140 formed on an outer peripheral surface thereof. For example, the indicia 140 can be formed as numbers from 0 to 9. A resilient advancement arm 142 extends from an upper surface of the first indicator member. The arm has a curved, circumferential shape and includes an tooth 144 or protuberance extending radially inward. The first indicator member further includes a circumferential driven gear 146 formed on a bottom of the first indicator member and configured with a plurality of teeth 148, preferably ten.

Figure 10:
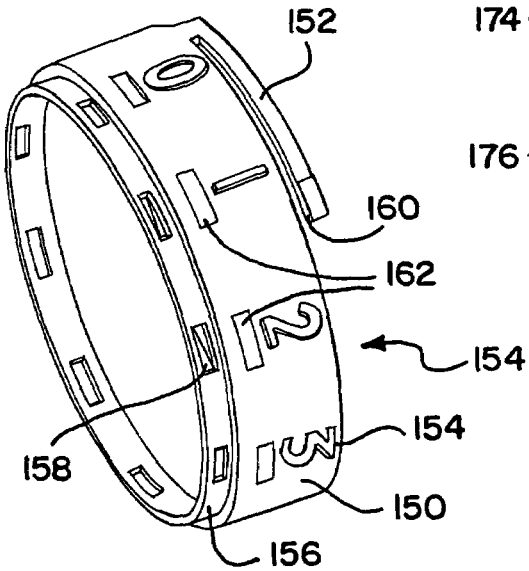
FIG. 10 is a bottom perspective view of a second indicator member.
Figure 12:
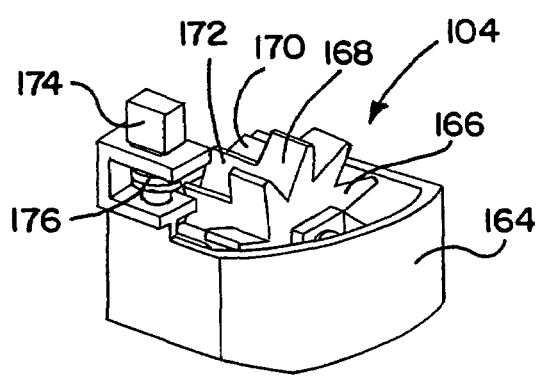
FIG. 12 is a perspective view of an actuator portion of the dose indicating device.

A second indicator member 134, shown in FIG. 10, includes a first circumferential skirt 150 with indicia 154 formed on an outer peripheral surface thereof. For example, the indicia can be formed as numbers from 0 to 9. A resilient advancement arm 152 extends from an upper surface of the second indicator member. The arm has a curved, circumferential shape and includes an tooth or protuberance 160 extending radially inward. A second circumferential skirt 156 extending from a bottom of the first skirt 150 and having a smaller outer diameter than the first skirt defines a drive portion of the second indicator member. A plurality of first and second indentations 162, 158 or slots are spaced circumferentially around the first and second skirts 150, 156 respectively.

As shown in FIGS. 4 and 5, the arms of the collar 112 extend through openings 113 (FIG. 9) formed in the top of the first indicator member, with the hooks 114 engaging a bottom surface of the top thereof. A lower second indicator member 134 is positioned on top of the first indicator member 132, with the slots 162 formed in the first skirt 150 indexed on the lower indexing portions 124, and in particular the bumps 126, formed on the interior of the housing. An upper second indicator member 134 (otherwise referred to as a third indicator member) is positioned on the top of the lower second indicator 134 member, with the slots 162 formed in the first skirt 150 indexed on the upper indexing portions 124, and in particular the bumps 126, formed on the interior of the housing 108. In this way, the second indicator members 134 are secured to the housing 108 by way of the indexing members and hold the first indicator member 132 against the bottom lip 130 thereof. The container 12 and collar 106, however, are moveable in the longitudinal direction relative to the housing 108 and indicator members 132, 134, with the arms 112 of the collar moving through the openings formed in the first indicator member 132 as the container 12, and in particular the valve stem 18, is moved between an extended position and depressed position.

Referring to FIGS. 1, 3-5, 12 and 16, the actuator portion 104 of the indicating device includes a housing 164 that is disposed in the bottom of the cavity 202 between the wall of the dispenser housing and the support block 212. The actuator housing 164 can be connected to the dispenser housing with adhesive, welding, snap fit, mechanical fasteners, other known fastening devices and/or combinations thereof. When the container is installed in the dispenser housing 200, the bottom of the indicator housing ring 130 rests on top of the actuator housing 164. In an alternative embodiment, the actuator housing 164 is formed integrally as part of the dispenser housing 200.

In another embodiment, the actuator portion is also connected to and removeable with the container as it is moved to the disengaged position. In particular, the actuator housing is integrally formed with the indicator portion housing.

The actuator portion includes a drive gear 166 rotatably mounted in the actuator housing, preferably about an axis substantially perpendicular to the longitudinal axis 215. The drive gear 166 has a plurality of drive teeth 168 formed around the periphery thereof that are engaged with the driven teeth 148 of the first indicator member 132. A ratchet gear 170 is coaxially mounted with the drive gear 168 and includes a plurality of ratchet teeth 142. The ratchet gear is preferably integrally molded with the drive gear. Alternatively, the ratchet gear and drive gear are formed as a single gear. An actuator member 174 is mounted to the actuator housing 164 and is moveable relative thereto in the longitudinal direction.

A spring 176 is captured by the housing and biases the actuator member 174 in an upward direction against the top of the container. A bottom end 175 of the actuator member 174 includes a hook portion or pawl that selectively engages at least one of the ratchet teeth 172. A non-return member 173 selectively engages another of the ratchet teeth 172 to allow for only one-way rotation of the ratchet gear 170 and associated drive gear 166. The top of the actuator member 174 is engaged with the bottom of the container.

In operation, the user moves the container 12 relative to the dispenser housing 200 so as to dispense a dose of substance. As the container 12 is moved downwardly along axis 215, the top of the container 12 engages the top of the actuator member 174 and moves the actuator member longitudinally against the biasing force of the spring 176 until the opposite end, or pawl, selectively engages at least one tooth 172 of the ratchet gear 170 and rotates the ratchet gear and connected drive gear an incremental amount. It should be understood that the actuator and non-return members can be configured such that the drive gear is rotated on the upstroke of the actuator (and the container relative to the housing) and is maintained in position by the non-return member upon the downstroke of the actuator (and container relative to the housing).

Upon each incremental movement (e.g., 36°) of the ratchet gear/drive gear 170, 166, which corresponds to a predetermined member of one movement of the container, the drive gear 166 engages at least one of the teeth 148 formed on the driven gear 146 of the first indicator member 132. The drive gear can be configured such that it engages the driven gear upon a predetermined number of actuations/movements of the container greater than one. For example, the ratchet teeth to drive gear teeth can have a ratio of greater than one, e.g. 10:1, such that the drive gear is driven an incremental amount upon ten (10) actuations of the container. As the drive gear 166 rotates the driven gear 146, the first indicator member 132 is rotated about the longitudinal axis 215 an incremental amount (e.g., 36°). It should be understood that the drive gear 166 can be provided with more or less drive teeth than the ratchet gear 170, such that the first indicator member 132 is moved more or less times relative to the number of longitudinal actuations of the container 12 respectively. As the first indicator member 132 is rotated, the indicia 140 visible through the corresponding viewing windows 120, 122 are changed so as to provide indicia to the user about the number of dosages of substance remaining in or dispensed from the container 12. In one preferred embodiment, the indicia 140 are configured as numbers, while in another embodiment the indicia are configured as a varying color pattern that gradually turns from green to red as the container is emptied. Of course, the indicia can be configured as various shading, segments, alpha-numeric characters and the like.

After the first indicator member 132 completes a single revolution, corresponding for example to ten (10) predetermined incremental rotational movements of the first indicator member, the end of the advancement arm 142 engages and is biased radially inward by the lower engagement portion 128 formed on the housing 108 until the protuberance 144 is engaged with one of the slots 158 formed in the lower driven portion of the lower second indicator member 134. As the first indicator member 132 is moved by the drive gear 166 of the actuator portion, the advancement arm 142 rotates the lower second indicator member 134 an incremental amount (e.g., 36°). As the lower second indicator member 134 completes a revolution, corresponding for example to ten (10) incremental rotational movements of the lower second indicator member, the advancement arm 152 of the lower second indicator member is biased radially inwardly by the upper engagement portion 128 on the housing and rotates the upper second indicator member 134 in the same manner. In this way, the indicia 140, 162 on the three indicator members 132, 134 are changed upon each actuation of the container to indicate the number of doses of substance that have been dispensed from or remain in the container.

Importantly, the container 12 and collar 106 move relative to the dispenser housing 200, the indicator portion housing 108 and the indicating members 132, 134 as the container 12 is moved along the longitudinal axis 215 between the extended and depressed position, such that the indicating members 132, 134 remain visible in the viewing window 122 during the entirety of each actuation of the container and do not move longitudinally relative thereto.

In addition, however, the container 12 with the indicator portion 102, including the collar 106 capturing the first indicator member 132, the housing 108 and indicator members 134, can be moved from an engaged position, wherein the valve stem 18 is disposed in the support block 212, and a disengaged position, wherein the container 12 and indicator portion 102 are disconnected from the dispenser housing 200 and actuator portion 104. In this way, the container 12 can be removed from the dispenser housing 200 for cleaning and the like, but with the indicator portion 102 being maintained with the container 12 such that the integrity of the dose count is maintained.

In a second embodiment of the invention, shown in FIGS. 13-15, the indicator portion 178 includes a collar 180 mounted to the end of the container 12 as explained above. The collar includes a downwardly extending frame 182. A liquid crystal display (LCD) screen 184, defined as an indicator member, is moveably, preferably slideably, mounted in the frame and is moveable relative thereto along the longitudinal axis 215. Alternatively, an LED screen can be used. The LCD screen 184 has indicia visible thereon that are visible through a window 186 formed in the dispenser housing.

The actuator portion 188 of the indicating device includes a printed circuit board (PCB) 190 with a base battery 188 and a switch 192. The frame 182 is moveably within a slotted cavity 194 formed in the actuator portion, with the LCD screen 184 being connected to the PCB when the container is in the engaged position. In particular, connectors (not shown), made for example of exposed metal conductor, on the PCB 190 and LCD 184 are coupled when the LCD 184 is snapped/inserted into the slot 194. Accordingly, as the container 12 and frame 182 are moved relative to the dispenser housing 200 and actuator portion 188, the LCD screen 184 is moved relative to the container 12 and remains stationary relative to the window 186 such that the indicia remain visible to the user. The container 12 engages the switch 192 and effects a change of indicia on the display screen 184. In particular, upon actuation of the switch 192, a signal is sent to the LCD to change the number displayed thereby.

The container 12 with the indicator portion 178, including the collar 180 capturing the LCD screen 184, can be moved from an engaged position, wherein the valve stem 18 is disposed in the support block 212, and a disengaged position, wherein the container 12 and indicator portion 178 are disconnected from the dispenser housing 200 and actuator portion 188. In this way, the container 12 can be removed from the dispenser housing 200 for cleaning and the like, but with the indicator portion 178 being maintained with the container 12 such that the integrity of the dose count is maintained.

In another aspect, the device is configured as one or more kits, which can include one or more of the dispenser housing 200, the container 12, the indicator portion 102, 178 and/or the actuator portion 104, 188.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A dispenser assembly:
   a dispenser housing;
   a container comprising an end portion and a valve moveable between a closed position and an open position, said container dispensing metered dosages of substance when said valve is moved to said open position, wherein said container is moveable relative to said dispenser housing between an engaged position and a disengaged position, wherein said container is removeably connected to said dispenser housing and is moveable relative to said dispenser housing along a longitudinal axis when in said engaged position, and wherein said container is disconnected from said dispenser housing when in said disengaged position;
   an indicating device comprising an indicating portion and an actuator portion, wherein at least said indicating portion is moveable with said container between said engaged and disengaged positions, and wherein said indicating portion comprises at least one indicator member, wherein said container is moveable relative to said at least one indicator member along said longitudinal axis when said container is in said engaged position.

2. The dispenser assembly of claim 1 wherein said container comprises a valve stem connected to said dispenser housing and moveable between a closed position and open position corresponding to said closed and open positions of said valve.

3. The dispenser assembly of claim 1 wherein said at least one indicator member is moveably secured to said container adjacent said end portion.

4. The dispenser assembly of claim 1 wherein said at least one indicator member is rotatably moveable about said longitudinal axis.

5. The dispenser assembly of claim 4 wherein said at least one indicator member comprises a plurality of indicator members.

6. The dispenser assembly of claim 5 wherein said plurality of indicator members comprises at least first, second and third indicator members, wherein said actuator portion is selectively engaged with said first indicator member upon a first predetermined number of reciprocal movements of said container relative to said dispenser housing along said longitudinal axis, wherein said first indicator member is selectively engaged with said second indicator member upon a predetermined number of incremental rotational movements of said first indicator member and wherein said second indicator member is selectively engaged with said third indicator member upon a predetermined number of incremental rotational movements of said second indicator member.

7. The dispenser assembly of claim 6 wherein said first predetermined number is one and wherein said predetermined number of incremental rotations movements of each of said first and second indicator members is ten.

8. The dispenser assembly of claim 1 wherein said indicator member comprises a liquid crystal display.

9. The dispenser assembly of claim 1 wherein said indicating portion comprises a collar secured to said end portion of said container.

10. The dispenser assembly of claim 9 wherein said at least one indicator member is retained by said collar and further comprising a housing, said housing comprising an indexing portion releasably engaging said at least one indicator member, wherein said container and said collar are moveable relative to said at least one indicator member and said housing along said longitudinal axis.

11. The dispenser assembly of claim 10 wherein said at least one indicator member comprises at least one first indicator member having an advancement member and at least one second indicator member having an drive portion, wherein said at least one first and second indicator members are each rotatably mounted about said longitudinal axis, and wherein said housing comprises an engagement portion selectively biasing said advancement member into engagement with said drive portion as said at least one indicator member is rotated about said longitudinal axis.

12. The dispenser housing of claim 1 wherein said actuator portion is connected to said dispenser housing and remains connected thereto as said container and said indicating portion are moved from said engaged position to said disengaged position.

13. The dispenser assembly of claim 12 wherein said actuator portion comprises a drive gear and wherein said at least one indicator member comprises a driven gear selectively engaged by said drive gear.

14. An indicating device kit suitable for indicating the number of metered dosages that have been dispensed from or remain in a container, said kit comprising:
    an indicating portion comprising a collar adapted to be mounted to the container and at least one indicator member connected to said collar and moveable relative thereto along a longitudinal axis; and
    an actuator portion separate from said indicating portion and adapted to advance said at least one indicator member.

15. The indicating kit of claim 14 wherein said indicating portion further comprises a housing comprising an indexing portion releasably engaging said at least one indicator member.

16. The indicating kit of claim 15 wherein said at least one indicator member comprises at least one first indicator member having an advancement member and at least one second indicator member having an drive portion, wherein said at least one first and second indicator members are each rotatably mounted about said longitudinal axis, and wherein said housing comprises an engagement portion selectively biasing said advancement member into engagement with said drive portion as said at least one indicator member is rotated about said longitudinal axis.

17. The indicating kit of claim 16 wherein said actuator portion comprises a drive gear and wherein said at least one first indicator member comprises a driven gear selectively engaged by said drive gear.

18. The indicating kit of claim 14 wherein said at least one indicator member is rotatable about said longitudinal axis.

19. The indicating kit of claim 14 wherein said at least one indicator member comprises a plurality of indicator members.

20. The indicating kit of claim 19 wherein said plurality of indicator members comprises at least first, second and third indicator members, wherein said actuator portion is selectively engageable with said first indicator member, wherein said first indicator member is selectively engageable with said second indicator member and wherein said second indicator member is selectively engageable with said third indicator member.

21. The indicating kit of claim 14 wherein said at least one indicator member comprises a liquid crystal display.

22. An indicating device suitable for indicating the number of metered dosages that have been dispensed from or remain in a container, said indicating device comprising:
  means for mounting at least a portion of said indicating device to the container; and
  means for indicating the number of metered dosages that have been dispensed from or remain in the container, wherein said means for indicating is connected to said means for mounting and is moveable relative thereto along a longitudinal axis.

* * * * *